United States Patent [19]

Mori et al.

[11] 4,366,161

[45] Dec. 28, 1982

[54] NICOTINAMIDE DERIVATIVE, PROCESS FOR PREPARING THE SAME AND PHARMACEUTICAL COMPOSITION CONTAINING THE SAME

[75] Inventors: Takashi Mori, Ohizumigakuenmachi; Sakae Takaku, Ageo; Fumiaki Matsuura, Tokyo; Yasushi Murakami, Tokyo; Yukifumi Noda, Tokyo; Tamotsu Yamazaki; Tomohiro Neichi, both of Tokorozawa; Hiroshi Nakakimura, Kamakura; Shigeyuki Kataoka, Saitama; Takashi Matsuno, Omiya; Shun-ichi Hata, Yokohama; Shigeru Takanashi, Asaka, all of Japan

[73] Assignee: Chugai Seiyaku Kabushiki Kaisha, Tokyo, Japan

[21] Appl. No.: 207,443

[22] Filed: Nov. 17, 1980

[30] Foreign Application Priority Data

Nov. 22, 1979 [JP] Japan ................................ 54-150674

[51] Int. Cl.$^3$ .................. C07D 213/56; A61K 31/455
[52] U.S. Cl. ..................................... 424/266; 546/262
[58] Field of Search ................ 546/255, 262; 424/263, 424/266

[56] References Cited

U.S. PATENT DOCUMENTS

3,786,058  1/1974  Edwards .......................... 546/255 X
3,875,174  4/1975  Edwards .......................... 546/255 X

FOREIGN PATENT DOCUMENTS

1339764 12/1973 United Kingdom ................ 546/255

OTHER PUBLICATIONS

C.A., 94:139627u, Chugai (1980).
C.A., 59, Grudzinski et al., 7476f (1963).
C.A. 67, Ojima et al., 7591k (1967).
Weygand et al., "Preparative Organic Chemistry", 1972, John Wiley & Sons, N.Y., pp. 464–467, 484–485, 488–489.

*Primary Examiner*—Joseph Paul Brust
*Attorney, Agent, or Firm*—Browdy and Neimark

[57] ABSTRACT

Novel compound, 1,2-bis(nicotinamido)propane and its pharmaceutically acceptable salts, a process for preparing the same and a pharmaceutical composition containing the same as an active ingredient are disclosed.

The compound acts to prevent or spasmolyse cerebral vasospasms, to prevent cerebral apoplexy and to lower the lipoperoxide level in blood.

14 Claims, No Drawings

NICOTINAMIDE DERIVATIVE, PROCESS FOR PREPARING THE SAME AND PHARMACEUTICAL COMPOSITION CONTAINING THE SAME

This invention relates to a nicotinamide derivative especially, 1,2-bis(nicotinamido)propane and its pharmaceutically acceptable salts, and a process for preparing the same and a pharmaceutical composition containing the same as an active ingredient.

There are still many deaths resulting from vascular disease such as arteriosclerosis, thrombosis, or the like and, therefore, the development of a medicine with an improved activity against such kind of disease is desired.

On the other hand, the fact that cerebral blood vessels of a cerebral hemorrhaged patient have spasms several days or several weeks after the hemorrhage has been attracting attention for years in the field of cerebral and neurosurgery. Such cerebral blood vessel spasms often cause serious cerebral damage.

The exact cause of cerebral vasospasms has not been clarified yet. It is assumed, however, that they are triggered by the action of a certain ingredient in arterial blood, or its denatured substance formed when the blood is blended with cerebrospinal fluid upon cerebral damage caused by traffic accident, subarachnoidal hemorrhage, or the like. In any case, no effective means of prevention, treatment, or spasmolysis of the symptom has been found yet and, therefore, development of an effective means is still desired.

In order to find such an effective means for preventing cerebral vasospasms, the inventors synthesized and screened various compounds and finally found that out of many analogous nicotinamido derivatives, 1,2-bis(-nicotinamido))propane was especially good pharmacological activities. After further tests on the compound, the inventors completed this invention.

1,2-Bis(nicotinamido)propane, the object compound of this invention can be prepared for example by condensing nicotinic acid or its reactive derivative at its carboxyl group with 1,2-diaminopropane under the conditions usually used in a typical acid amide-formation reaction. The reactive derivatives of nicotinic acid include; acid halides such as acid chloride; acid anhydride; mixed acid anhydrides such as those with carbonic acid, sulfuric acid, or phosphoric acid; and esters such as lower alkyl esters.

In this explanation, nicotinic acid and its reactive derivatives are referred to simply as nicotinic acid compound.

The reaction is usually carried out in an inert solvent such as pyridine, tetrahydrofuran, dioxane or the like. However, when the reactive derivative is a lower alkyl ester, the reaction is preferably conducted without solvent.

On the other hand, when acid chloride is used as the reactive derivative, the reaction is preferably carried out in the presence of a basic reaction accelerator such as triethylamine.

Although the reaction temperature is not critical, it usually ranges from $-10°$ to $150°$ C., more preferably from $-5°$ to $10°$ C. As an exception, if the reactive derivative is a lower alkyl ester, the reaction is preferably effected at a relatively high temperature, such as at $100°$ to $130°$ C.

In order to obtain the product in a good yield, an excess amount of nicotinic acid compound is used. More preferably, the molar amount of the reactant used is 2.3–5 times as much as the diamine which is another reactant.

The thus synthesized 1,2-bis(nicotinamido)propane acts to prevent or spasmolyse vasospasms induced by various causes. Also, even a small dose of the compound acts to prevent death from cerebral apoplexy experimentally induced by administration of arachidonic acid and to lower the lipoperoxide level in blood.

On the other hand, the compound in question has a desirable physiological activity on the prostaglandin formation system in vivo, in that it increases the formative ratio of prostaglandin $I_2$ to thromboxane $A_2$ ($I_2/A_2$).

The compound of this invention has low toxicity, its acute toxicity being more than 1,000 mg/kg in the standardized acute toxicity test using mice.

The compound of this invention is formulated in the conventional pharmaceutical manner into a desired form such as tablet, granule, powder, capsule for oral administration or as an injection for parenteral administration.

Examples of pharmaceutical carriers preferred for formulating a preparation for oral administration include lactose, starch, dextrin, sucrose, crystalline cellulose, kaolin, calcium carbonate, talc, magnesium stearate and the like. On the other hand, in formulating a preparation to be injected, distilled water and an aqueous solution of sodium chloride, potassium chloride or other proper salt are preferred.

The dosage of the pharmaceutical preparation of this invention usually ranges from 0.1 to 2,000 mg/day, more preferably from 5 to 500 mg/day.

The pharmacological activities of the compound of this invention are shown in the results of the following Experiments. In the experiments, compounds which represented by the formulae I, II and III were also tested for comparison.

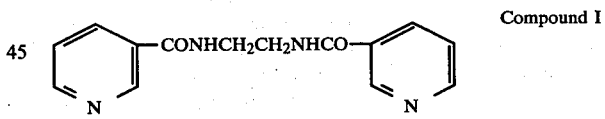

Compound I

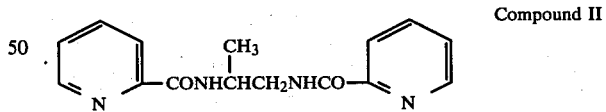

Compound II

Two compounds which are very close in structure to the compound of this invention are reported in Chemical Abstract 59 7476f; and ibid. 67 7591k; respectively.

However, no medical utility has been reported for either of the compounds, and, according to the following Experiments made by the inventors, no useful and significant pharmacological activity was confirmed.

Similarly, the compound III of the formula

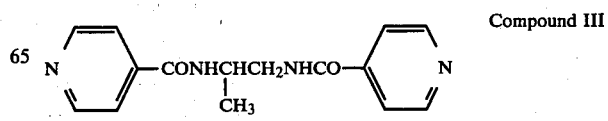

Compound III which was synthesized by the inventors and is very close in chemical structure to the compound of this invention exhibits extremely poor pharmacological activity.

EXPERIMENT 1

Sprague Dawley-strain male rats weighing 200–250 g were orally administered each of the listed compounds below, and 30 minutes after the administration, arachidonic acid was injected concurrently to blood flow under anesthesia into the left carotid artery of each in a dose of 20 mg/kg. One hour after the injection, the dead rats were counted. The results are shown in the following Table.

| Test Compound | Dose (mg/kg) | Number of Rats Dead/Tested |
|---|---|---|
| Control | — | 6/6 |
| Compound of This Invention | 200 | 0/5 |
| Compound of This Invention | 100 | 0/5 |
| Compound I | 200 | 3/5 |
| Compound II | 200 | 1/5 |
| Compound II | 100 | 4/5 |
| Compound III | 200 | 3/5 |

EXPERIMENT 2

A solution of the test compound (10 μl) was added to one ml of a mixture containing 0.9 mg of pig aortic microsomes and $9 \times 10^8$ rat platelets and the mixture was allowed to stand for 3 minutes at 23° C. Then, 10 μl of [1-$C^{14}$]—arachidonic acid (80 nM, 4.8 Ci/mol) in 0.1 M sodium bicarbonate aqueous solution was added to the mixture to initiate the reaction at 23° C. for 3 minutes, after which the reaction was terminated by the addition of 50 μl of 0.5 M citric acid aqueous solution, and the mixture was extracted with 8 ml of ethyl acetate. The organic layer was recovered, and concentrated to dryness under reduced pressure. The residue was dissolved in 100 μl of ethyl acetate and subjected to thin-layer chromatography using a silica gel glass plate and as a developing solvent, isooctane/ethyl acetate/acetic acid/water (5:11:2:10, upper phase).

After the developing, the plate used was scanned for radioactivity and areas corresponding to radioactive bands of thromboxane $B_2$ (TXB$_2$) and 6-keto-prostaglandin $F_{1\alpha}$ (6-keto-PGF$_{1\alpha}$) were scraped to recover the silica gel and counted by a liquid scintillation counter. The conversions of arachidonic acid used to TXB$_2$ or to 6-keto-PGF$_{1\alpha}$ was calculated and the amount each of TXB$_2$ and 6-keto-PGF$_{1\alpha}$ was determined.

Under the conditions described above, all of the TXA$_2$ and PGI$_2$ appeared to be converted into TXB$_2$ and 6-keto-PGF$_{1\alpha}$, respectively. Thus, it can be assumed that the amounts of TXB$_2$ and 6-keto-PGF$_{1\alpha}$ were equated with those of TXA$_2$ and PGI$_2$ formed in the reaction system.

The ratio of PGI$_2$ to TXA$_2$ on each of the test compound is shown in the following Table. The final concentration of the test compound was adjusted to $5 \times 10^{-4}$ M in all of the runs.

| Test Compound | $I_2/A_2$ |
|---|---|
| Control | 0.27 |
| Compound of This Invention | 1.40 |
| Compound I | 0.87 |
| Compound II | 0.54 |
| Compound III | 0.88 |

EXPERIMENT 3

A Siamese cat weighing 2–2.5 kg was anesthetized and its head was immobilized with a stereotaxic apparatus by fixing the cat on its back. The neck was cut open and its windpipe and esophagus and skull were excised to expose the cerebral basilar arteries. One ml of arterial blood previously extracted from the same cat and allowed to stand for a week at 37° C. was poured onto the basilar arteries. Ten minutes after pouring, the blood was removed by suction, and one ml of an aqueous solution (pH 7.5 to 8.0) containing 0.5 mg of the test compound was poured onto the same portion. Again, ten minutes after pouring of the test compound solution, the solution was removed by suction, and percent spasmolysis of the arteries which had been under the condition of spasm was measured.

The test results show that the compound of this invention gave 82% spasmolysis, while the compound I exhibited only 30% spasmolysis.

EXPERIMENT 4 ddY-Strain male mice were divided into groups of 10 members each and not fed for 16 hours. Then aqueous alloxan was intravenously administered through the tail vein in a dose of 75 mg/kg in terms of alloxan. The compound of this invention or the compound II was orally administered twice, each dose being 200 mg/kg, 24 and 30 hours after the administration of alloxan, and 48 hours after the administration, blood was sampled and the lipoperoxide level of the blood plasma was measured by Lipoperoxide-Test Wako to obtain the TBA value.

The mean TBA-value of each of the test groups was compared with the mean value of the control groups to which no test compound was given. The compound II exhibited a 20% drop, in contrast, the compound of this invention had about a 40% drop.

EXAMPLE 1

Nicotinyl chloride hydrochloride (25 g) was added to a mixture of 1,2-diaminopropane (4.7 g), pyridine (200 ml) and triethylamine (50 ml) under cooling with ice while stirring and, after stirring for an hour, water (400 ml) was added to the mixture, followed by concentrating it under reduced pressure. To the residue were added water and then potassium carbonate to subject the residue to salt out while extracting with tetrahydrofuran. The tetrahydrofuran layer recovered was dried over potassium carbonate and then concentrated. The oily residue was passed through a column filled with silica gel to purify it. Recrystallization from ethyl acetate gave 1,2-bis(nicotinamido)propane having a melting point of from 156°–157° C.

Analysis: Clcd. for $C_{15}H_{16}N_4O_2$: C, 63.4; H, 5.7; N, 19.7 (%) Found: C, 63.2; H, 5.9; N, 19.5 (%)

EXAMPLE 2

Ethyl chloroformate (12.5 g) was added dropwise to a mixture of nicotinic acid (15.4 g), triethylamine (12.6 g) and tetrahydrofuran (500 ml) under cooling with ice while stirring, and after stirring the mixture for another 30 minutes, 1,2-diaminopropane (3.7 g) was added at one time followed by stirring at room temperature for an hour. Water (300 ml) was added to the mixture and, while salting out with potassium carbonate, extracted with tetrahydrofuran.

The extract was treated as in Example 1 to give 10 g of product, which showed no drop in melting point after mixing the product with that given in Example 1, and it had the same elementary analysis value as those in Example 1.

EXAMPLE 3

A mixture of 1,2-diaminopropane (2 g) and methyl nicotinate (12 g) was heated at a temperature between 100° and 120° C. for 3–5 hours while distilling producing methanol off from the reaction system. Then, after cooling the mixture by allowing it to stand, the product was purified through chromatography with silica gel and crystallizing from ethyl acetate to give 3 g of the product.

The product did not show any drop in melting point when mixing it with the product of Example 1, and its elementary analysis value was the same as that of Example 1.

EXAMPLE 4

The compound prepared in Example 1 (4 g) was dissolved in distilled water to form 2 l of the solution. The solution was filtered through filter paper and then through a membrane filter with 0.45μ pores, put into brown-colored ampules in a volume of 2 ml per ampule. Each ampule was purged with nitrogen gas. Immediately after purging with nitrogen gas, each ampule was sealed and then sterilized in an oven at 121° C. for 20 minutes to give ampules for injection.

EXAMPLE 5

The product of Example 1 (60 g), lactose (250 g), crystalline cellulose (72 g), corn starch (14 g) and magnesium stearate (4 g) were pulverized and thoroughly blended and shaped with a tableting machine into tablets, each 8 mm in diameter and 200 mg in weight, for oral administration.

What is claimed is:

1. 1,2-Bis(nicotinamido)propane and its pharmaceutically acceptable salt.

2. A pharmaceutical composition comprising a pharmaceutically active amount of 1,2-bis(nicotinamido)propane or a pharmaceutically acceptable salt thereof, and a pharmaceutically acceptable carrier.

3. A pharmaceutical composition according to claim 2 wherein said 1,2-bis(nicotinamido)propane is present in the composition in such an amount that the active compound is administered in an amount of from 0.1 to 2,000 mg per day.

4. A pharmaceutical composition according to claim 2 wherein said administration amount of the active compound is between 5 and 500 mg per day.

5. A pharmaceutical composition according to claim 2 wherein said composition is in the form for oral administration selected from the group consisting of tablet, granule, powder, and capsule.

6. A pharmaceutical composition according to claim 5 wherein said carrier is selected from the group consisting of lactose, starch, dextrin, crystalline cellulose, kaolin, calcium carbonate, talc and magnesium stearate.

7. A pharmaceutical composition according to claim 2 wherein said composition is in the form for parenteral administration.

8. A pharmaceutical composition according to claim 7 wherein said carrier is selected from the group consisting of distilled water, sodium chloride aqueous solution, and potassium chloride aqueous solution.

9. A method for treating a vascular disease which comprises administering to a patient in need of said therapy an amount effective for said therapy of a compound according to claim 1.

10. A method according to claim 9, wherein the composition is administered in an amount of from 0.1 to 2,000 mg per day of the pharmaceutically active compound.

11. A method according to claim 9, wherein the composition is administered in an amount of from 5 to 500 mg per day of the pharmaceutically active compound.

12. A method according to claim 9, wherein said vascular disease is thrombosis.

13. A method according to claim 9, wherein said vascular disease is arteriosclerosis.

14. A method according to claim 9, wherein said vascular disease is cerebral vasospasm.

* * * * *